US009220475B2

(12) United States Patent
Klodell et al.

(10) Patent No.: US 9,220,475 B2
(45) Date of Patent: Dec. 29, 2015

(54) ACOUSTIC SYSTEM FOR MONITORING THE PERFORMANCE OF LEFT VENTRICLE ASSIST DEVICES AND OTHER MECHANICAL DEVICES IMPLANTED IN A PATIENT'S BODY

(75) Inventors: Charles T. Klodell, Gainesville, FL (US); Nikolaus Gravenstein, Gainesville, FL (US); Wilhelm K. Schwab, Gainesville, FL (US)

(73) Assignee: UNIVERSITY OF FLORIDA RESEARCH FOUNDATION, INC., Gainesville, FL (US)

( * ) Notice: Subject to any disclaimer, the term of this patent is extended or adjusted under 35 U.S.C. 154(b) by 1108 days.

(21) Appl. No.: 13/264,269
(22) PCT Filed: Apr. 14, 2010
(86) PCT No.: PCT/US2010/031042
§ 371 (c)(1),
(2), (4) Date: Dec. 15, 2011
(87) PCT Pub. No.: WO2010/120887
PCT Pub. Date: Oct. 21, 2010

(65) Prior Publication Data
US 2012/0083682 A1 Apr. 5, 2012

Related U.S. Application Data
(60) Provisional application No. 61/169,583, filed on Apr. 15, 2009.

(51) Int. Cl.
*H04R 29/00* (2006.01)
*A61B 7/00* (2006.01)
(Continued)

(52) U.S. Cl.
CPC .............. *A61B 7/005* (2013.01); *A61B 7/026* (2013.01); *A61B 8/0833* (2013.01); *G01S 5/22* (2013.01)

(58) Field of Classification Search
CPC ... H04W 64/00; H04W 64/02; H04W 64/008; H04W 64/027; H04W 64/028; H04W 64/023; H04W 64/021; H04W 88/08; H04W 12/12; G06F 17/3074; G06F 17/30241; G06F 3/165; G06F 3/017; G06F 3/0414; G06F 3/0484; G06F 19/3481; G06F 19/3437; A61B 5/0205; A61B 5/02055; A61B 5/021; A61B 5/0456; A61B 7/003; A61B 2018/00351; H04R 1/1041; H04R 1/08; H04R 1/1091; H04R 2420/07; H04R 2499/11; H04R 29/00; H04R 3/00; H04R 3/005; H04R 3/02; H04R 17/02; H04R 19/04; H04R 1/04; H04R 1/222; H04R 1/32; H04R 1/326; H04R 1/406; H04M 2250/12; H04M 2250/04; H04M 1/0202; G10K 2210/1081; G10K 11/004; G10K 11/178; G10K 2210/3028; G10K 2210/3045
USPC ........... 381/17, 18, 19, 23, 26, 56, 57, 58, 60, 381/61, 313, 314, 317, 321, 326, 71.1, 71.2, 381/71.11, 71.12, 71.14, 72, 73.1, 74, 77, 381/78, 80, 91, 92, 93, 94.1, 94.7, 95, 101, 381/102, 103, 111, 112, 113, 114, 122; 600/407, 485, 486, 508, 509, 514, 528, 600/586; 455/563, 456.1; 345/14.08, 14.01, 345/14.11; 700/94, 258
See application file for complete search history.

(56) References Cited

U.S. PATENT DOCUMENTS 5,844,997 A * 12/1998 Murphy, Jr. ..................... 381/92
5,938,602 A * 8/1999 Lloyd ........................... 600/424
(Continued)

OTHER PUBLICATIONS
International Search Report from International Application No. PCT/US2010/031042, mailed Nov. 22, 2010.
(Continued)

*Primary Examiner* — Leshui Zhang
(74) *Attorney, Agent, or Firm* — Alston & Bird LLP (57) ABSTRACT

Embodiments of the present invention are related to apparatus and methods for acoustically monitoring the performance of a medical device disposed within the body of a patient. According to one embodiment of an apparatus, the apparatus includes at least one acoustic sensor and a computer system that is connected to receive information from the acoustic sensor, wherein the acoustic sensor is adapted to receive a set of acoustic information that corresponds to acoustic activity within the body of said patient. The computer system is adapted for: (A) receiving the set of acoustic information, and (B) using the set of acoustic information to calculate location information relating to a location of a source of the acoustic activity.

20 Claims, 3 Drawing Sheets

(51) Int. Cl.
    *A61B 7/02*      (2006.01)
    *A61B 8/08*      (2006.01)
    *G01S 5/22*      (2006.01)

(56) References Cited

U.S. PATENT DOCUMENTS 7,576,642 B2 *    8/2009    Rodemer .................. 340/457.1

2004/0236239 A1    11/2004    Murray et al.

OTHER PUBLICATIONS

Slaughter, Mark S., et al.; "Utilization of Acoustic Signatures to Identify HeartMate XVE Device End-of-Life"; Journal of Heart and Lung Transplantation; Jun. 2007; pp. 579-583.

Kompis, Martin, et al.; "Acoustic Imaging of the Human Chest"; Chest, American College of Physicians; Downloaded from Chest Journal Jul. 24, 2007; pp. 1309-1321.

\* cited by examiner

ACOUSTIC SYSTEM FOR MONITORING THE PERFORMANCE OF LEFT VENTRICLE ASSIST DEVICES AND OTHER MECHANICAL DEVICES IMPLANTED IN A PATIENT'S BODY

CROSS REFERENCE TO RELATED APPLICATIONS

This application is a national stage application filed under 35 U.S.C. 371 of International Application No. PCT/US2010/031042, filed Apr. 14, 2010, which claims priority from U.S. Provisional Application No. 61/169,583, filed Apr. 15, 2009, each of which is incorporated herein in its entirety.

BACKGROUND

Left ventricle assist devices (LVAD's) are mechanical devices that are implanted into a patient's body to assist the function of the patient's heart. These devices often remain in place for an extended period of time that may approach the end of an LVAD's useful life. Currently, it is difficult to assess the mechanical state of an LVAD without accessing the LVAD using surgical procedures, which can be expensive, painful, and prone to risk.

Dr. Mark A. Slaughter et al. recently published an article on various techniques for utilizing acoustic signatures to identify the end of life of a particular type of LVAD, the Heartmate XVE. (This article is included as part of this disclosure—See Appendix A.) However, the apparatus described in the Slaughter article appears to be bulky, cumbersome, and may be prone to false alarms that are generated due to noise from sources within the patient's body other than the LVAD. Accordingly, there is a need for improved, more reliable, non-invasive procedures for assessing the mechanical state of LVAD's and other mechanical devices that are implanted within a patient's body.

BRIEF SUMMARY

Embodiments of the present invention are directed to apparatus and methods for acoustically monitoring the performance of a medical device (e.g., a left ventricle assist device) disposed within the body of a patient. According to one embodiment, the apparatus includes a plurality of acoustic sensors, wherein a first acoustic sensor is spaced apart from a second acoustic sensor, and a computer system that is connected to receive information from the first and second acoustic sensors. The apparatus may include more than two acoustic sensors, such as a third acoustic sensor, wherein the first, second, and third acoustic sensors may be positioned in a substantially triangular arrangement with respect to one another. The first acoustic sensor is adapted to receive a first set of acoustic information that corresponds to acoustic activity within the body of the patient, and the second acoustic sensor is adapted to receive a second set of acoustic information corresponding to the acoustic activity within the body of the patient. The computer system is adapted for: (A) receiving the first and second sets of information, and (B) using the first and second sets of information to calculate location information relating to a location of a source of the acoustic activity.

In one embodiment, the computer system is further adapted for using the location information to assess whether the source of the acoustic activity is the medical device. In addition, the computer system may be further adapted for comparing the first and/or second sets of acoustic information with acoustic information from within a library of acoustic information to assess a current mechanical state of the medical device, such as to assess whether the first and/or second sets of acoustic information is indicative of a current or impending mechanical malfunction of the medical device.

According to additional aspects of the apparatus, the computer system is configured for calculating the location information regarding the location of the source of the acoustic activity based, at least in part, on: (A) the first set of acoustic information; (B) the second set of acoustic information; and (C) information regarding a position of the first sensor relative to the second sensor. In one embodiment, the apparatus is a belt, and the first and second acoustic sensors are attached adjacent the belt. The belt may be adapted to be wrapped around the patient's body while the first acoustic sensor receives the first set of acoustic information and while the second acoustic sensor receives the second set of acoustic information. The belt may be adapted to maintain the first acoustic sensor in a fixed position relative to the second acoustic sensor while the first sensor receives the first set of acoustic information and while the second acoustic sensor receives the second set of acoustic information.

In an additional aspect, the acoustic sensors are configured to be attached adjacent to the belt in one of a plurality of positions. For example, the first acoustic sensor is adapted to be attached adjacent to the belt in a first position, wherein the belt includes a first set of one or more markings and/or target indicia adapted to facilitate the attachment of the first acoustic sensor adjacent the belt in the first position. The belt may include a second set of one or more markings and/or target indicia adapted to facilitate the attachment of the second acoustic sensor adjacent the belt in a second position. Moreover, the first acoustic sensor may include a window and a recticle disposed within the window, wherein the recticle is adapted to facilitate positioning of the first acoustic sensor in the first position by aligning at least a portion of the recticle with the first set of markings and/or target indicia. The second acoustic sensor may also include a window and a recticle, wherein the recticle is adapted to facilitate positioning of the second acoustic sensor in the second position by aligning at least a portion of the recticle with the second set of markings and/or target indicia.

According to an additional aspect, a method of determining information regarding the position of acoustic activity within a patient's body is provided. The method includes positioning a plurality of acoustic sensors such that a first acoustic sensor is in a first position relative to the patient's body and a second acoustic sensor is in a second position relative to the patient's body. The method further includes using the first sensor to retrieve a first set of acoustic information that corresponds to the acoustic activity and using the second sensor to retrieve a second set of acoustic information that corresponds to the acoustic activity. Furthermore, the method includes using the first and second sets of acoustic information, as well as location information regarding a position of the first sensor relative to the second sensor, to calculate information regarding a location of a source of said acoustic activity.

According to one embodiment, an apparatus for acoustically monitoring the performance of a medical device disposed within the body of a patient includes at least one acoustic sensor. The apparatus includes a computer system that is connected to receive information from the acoustic sensor, wherein the acoustic sensor is adapted to receive a set of acoustic information that corresponds to acoustic activity within the body of said patient. The computer system is adapted for: (A) receiving the set of acoustic information, and (B) using the set of acoustic information to calculate location information relating to a location of a source of the acoustic activity.

BRIEF DESCRIPTION OF THE DRAWINGS

Reference will now be made to the accompanying drawings, which are not necessarily drawn to scale, and wherein:

FIG. 3 is a graph of LVAD speed vs. time during the occurrence of a suction event within a Heartmate-II LVAD. To generate this figure, a patient with a HeartMate-II LVAD was seen for a routine clinic visit and an audio recording was made of his Heartmate-II LVAD. A distinct decrease in pitch was recorded, and subsequently analyzed by Fast Fourier Transform (FFT) of 1.31072 second segments, starting a new segment every 0.65536 seconds. In each time segment, the frequency corresponding to the maximum modulus of the FFT was identified among frequencies corresponding to between 8,000 and 10,000 RPM. The resulting frequency is taken as an estimate of the LVAD's speed in the respective time interval.

DETAILED DESCRIPTION OF VARIOUS EMBODIMENTS OF THE INVENTION

Various embodiments of the present invention will now be described more fully hereinafter with reference to the accompanying figures, in which some, but not all embodiments of the inventions are shown. Indeed, these inventions may be embodied in many different forms and should not be construed as limited to the embodiments set forth herein. Rather, these embodiments are provided so that this disclosure will satisfy applicable legal requirements. Like numbers refer to like elements throughout.

Brief Overview of Particular Embodiments of the Invention

Figure 1:
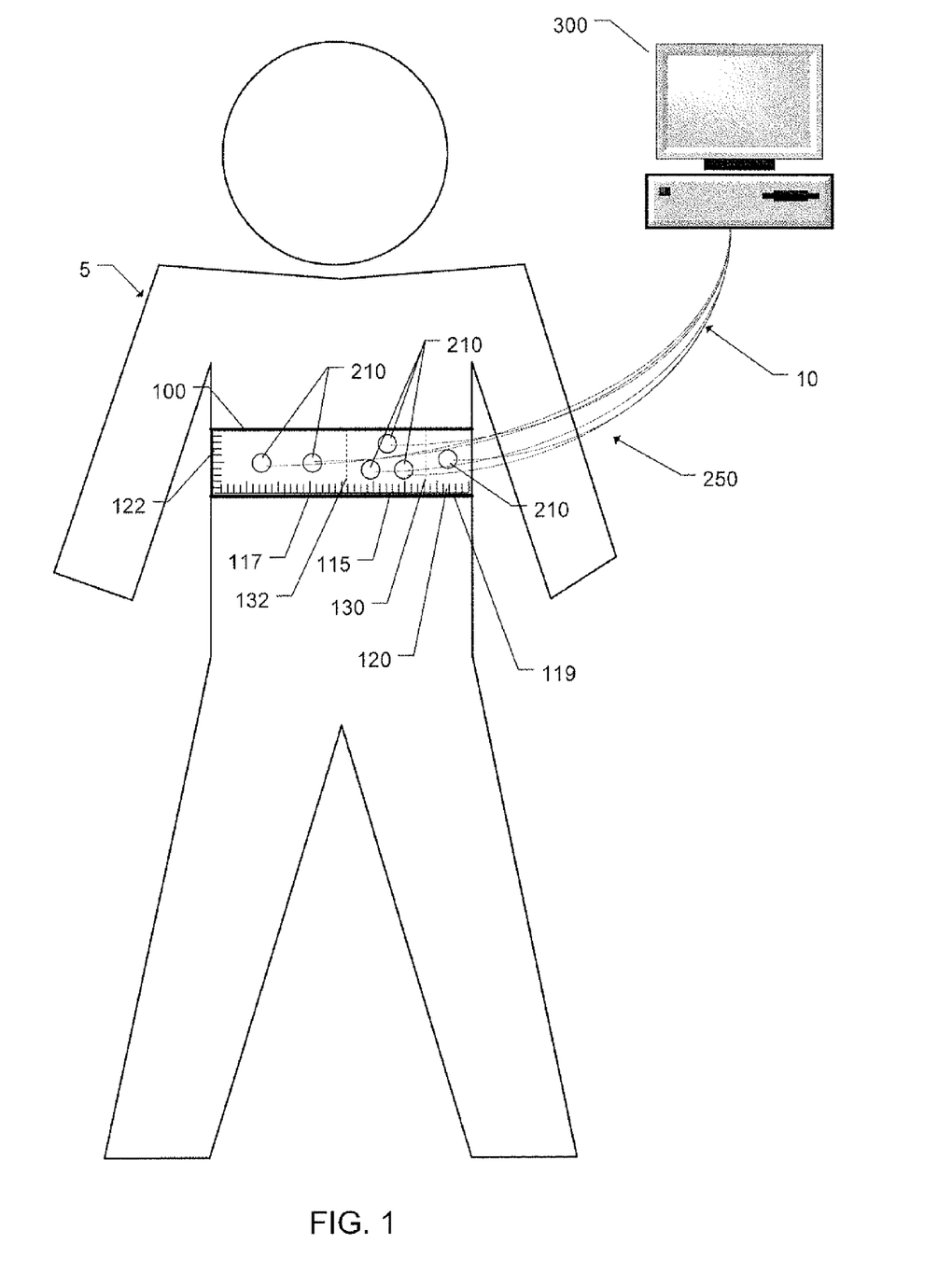
FIG. 1 is a schematic diagram of an acoustic monitoring system according to a particular embodiment of the invention. In this embodiment, a patient, on which the acoustic monitoring system is being used, is shown facing out of the drawing.

As shown in FIG. 1, an acoustic monitoring system 10 according to various embodiments of the invention includes multiple acoustic sensors 210 (e.g., electronic stethoscopes, hydrophones, or any other suitable acoustic sensors) that are used to at least substantially simultaneously (e.g., simultaneously) monitor sounds generated by a mechanical device (e.g., an LVAD) implanted within a patient's body. Data from the acoustic sensors 210 is then used to evaluate the performance of the mechanical device. For example, if the sound signature of sounds received by the acoustic sensors 210 corresponds to the sound signature of an LVAD that is close to failure, the system may generate a warning message indicating a potential problem with the LVAD. In addition, data from the acoustic sensors 210 may, in various embodiments, be used to learn more about the patient's physical condition.

In various embodiments, signals from the multiple acoustic sensors 210 may transmit, to a computer system 300 associated with the acoustic monitoring system 10, information regarding the sounds monitored by the acoustic sensors 210. The computer system 300 may then use this information, along with information regarding the relative positions of the acoustic sensors 210, to determine the general location of the source of the sounds. This information may be used to determine which of the sounds were generated, for example, by the LVAD, and which sounds were generated by the patient's body (e.g., the patient's intestines). This may be helpful in avoiding false alarms regarding the performance of the device. Thus, embodiments of the present invention provide a non-invasive and an easy to use system for monitoring the performance of a medical device, while also providing reliable data for assessing the performance of the medical device. In one embodiment, the acoustic information may be obtained from acoustic sensors 210 residing in a single plane (e.g., a belt) rather than employing complex three-dimensional algorithms or images to obtain such information.

The structure and function of various embodiments of the acoustic monitoring system 10 are described in greater detail below. It should be understood that the structure and techniques described in enclosed Appendix A may be used in various embodiments of the invention below. However, other embodiments may not incorporate the techniques or structure described in Appendix A.

Structure of Various Embodiments of the Acoustic Monitoring System

A particular embodiment of an acoustic monitoring system 10 is shown in FIG. 1. In this embodiment, the monitoring system 10 includes a plurality of acoustic sensors 210 (e.g., hydrophones or electronic stethoscopes—such as the ds32a electronic stethoscope by Thinklab) that are attached adjacent (e.g., to) a belt 100 that is adapted to be selectively wrapped around the torso of a patient 5. In particular embodiments, at least a portion of the belt 100 is adapted to be positioned proximate to the patient's LVAD (e.g., over the patient's chest, side, or upper abdomen), and the belt 100 is adapted to be maintained in a substantially fixed position relative to the patient's body by one or more suitable fasteners (e.g., a hook-and-loop fastening system, ties or snaps).

In the embodiment shown, the belt 100 includes a central support portion 115 that is adapted so that, when the belt 100 has been secured to the patient, the central support portion 115 is disposed immediately adjacent (e.g., over) the patient's LVAD (e.g., immediately adjacent an LVAD pocket that has been implanted in the patient). The belt 100 further includes a first lateral portion 117 that is configured to be selectively attached to a first lateral side of the central support portion 115 via a suitable fastener 132 (e.g., a zipper, a hook-and-loop fastening system, or snaps). The belt 100 also includes a second lateral portion 119 that is configured to be selectively attached to a second lateral side of the central support portion 115 via a suitable fastener 130 (e.g., a zipper, a hook-and-loop fastening system, or snaps). In particular embodiments, the belt's first and second lateral portions 117, 119 each include, adjacent their respective distal ends, at least a portion of a fastening system that is adapted to attach the distal end of the first lateral portion 117 to the distal end of the second lateral portion 119. This serves to maintain the belt 100 in a substantially fixed position relative to the patient's chest.

In the embodiment shown in FIG. 1, the central support portion 115 includes three acoustic sensors 210 that are each attached adjacent (e.g., to) the central support portion 115 and that are spaced apart from each other on the surface of the central support portion 115. As shown in FIG. 1, in particular embodiments, the three acoustic sensors 210 are positioned in a substantially triangular acoustic sensor arrangement. In various embodiments, the belt's central support portion 115 may include an orientation sensing device (e.g., an inclinometer) that is adapted to sense the orientation of the substantially triangular arrangement of acoustic sensors 210. In alternative embodiments, the system includes an input device (e.g., a switch or other input) that allows a user to manually input the orientation of the substantially triangular acoustic sensor arrangement into the system. For example, the input device may be a toggle switch that a user may move between:

(1) a first orientation to specify that the triangular acoustic sensor arrangement is pointing upwardly; and (2) a second orientation to specify that the triangular acoustic sensor arrangement is pointing downwardly.

Similarly, in various embodiments, the belt's first lateral support portion 117 includes at least one sensor 210 that is spaced apart from the sensors 210 that are disposed on the central support portion 115. In addition, the belt's second lateral support portion 119 may include one or more sensors 210 that are spaced apart from both the sensors 210 that are disposed on the belt's central support portion 115, and the sensors 210 that are disposed on the belt's first lateral support portion 117.

As shown in FIG. 1, when the belt's first and second lateral support portions 117, 119 are attached to respective opposite lateral sides of the belt's central support portion 115, and the respective distal ends of the belt's first and second lateral support portions 117, 119 are attached together, the belt 100 forms a continuous loop that encircles the patient's torso (e.g., the patient's upper, middle, or lower thoracic torso). As may be understood from FIG. 1, in various embodiments, a series of acoustic sensors 210 are positioned in various positions along the belt's circumference to provide for sampling (e.g., simultaneous sampling) of sounds at different positions along the patients' body.

Figure 2:
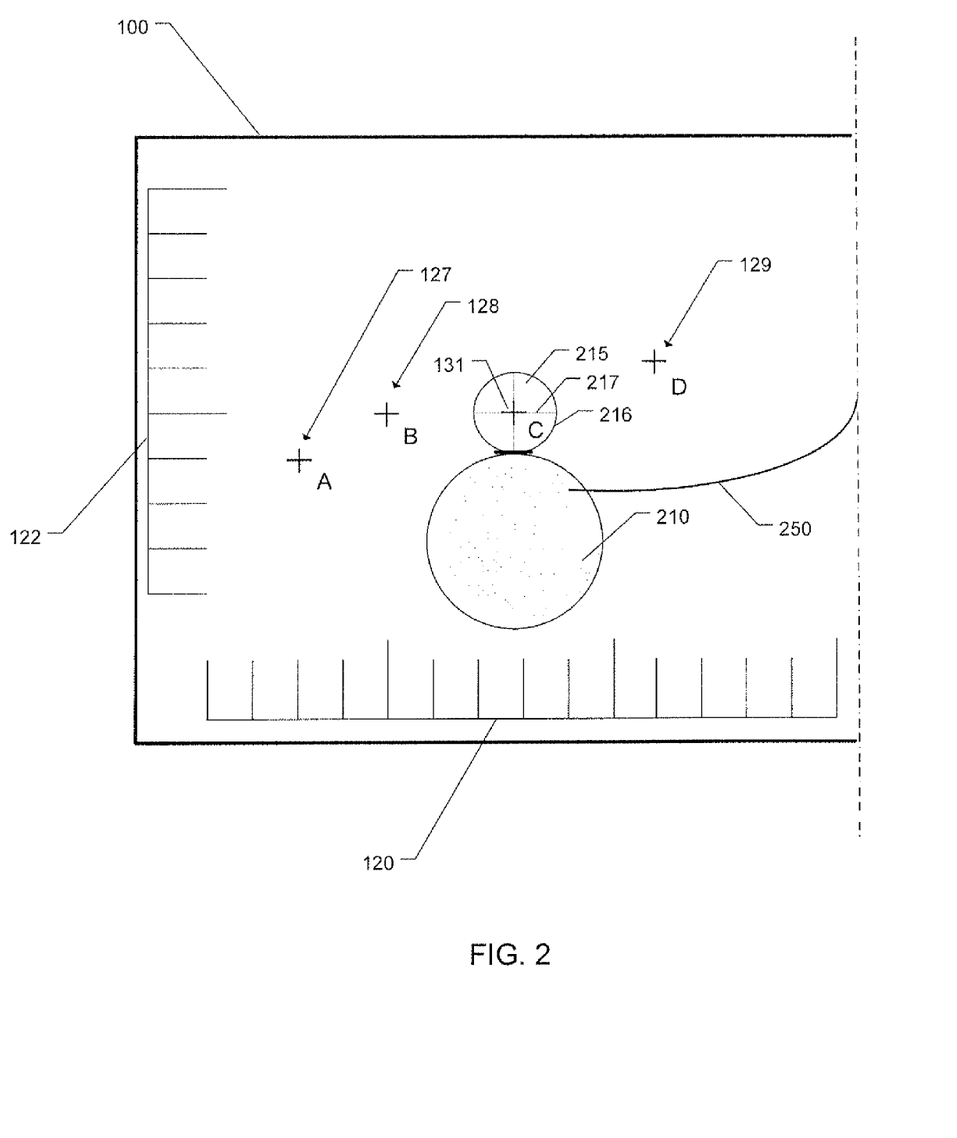
FIG. 2 is a detailed view of a portion of a belt used within various embodiments of the invention.

In particular embodiments, the acoustic sensors 210 and belt 100 may include fastening systems (e.g., hook-and-loop fastening systems or snaps) that are adapted to allow the acoustic sensors 210 to be easily detached from the belt 100 and reattached to the belt 100 at another position. Turning to FIG. 2, in various embodiments, the belt 100 may include graduated markings (e.g., vertical and/or horizontal graduated markings 120, 122), and/or target indicia 127, 128, 129, 131 for assisting a user in positioning acoustic sensors 210 adjacent the belt 100. In various embodiments, the belt is made at least partially of (and, in various embodiments, substantially entirely of) a substantially non-stretching material. This helps to maintain the graduated markings in a substantially fixed relation to each other. Also, in certain embodiments, the belt may include any suitable mechanism (e.g., a selectively releasable clip or buckle) for allowing users to selectively adjust the length of the belt 100.

In particular embodiments, one or more of the acoustic sensors 210 includes a sighting structure 216 that includes a window 215 and a recticle 217 that is overlaid onto the window 215. In particular embodiments, this sighting structure 216 is attached to an outer perimeter of the acoustic sensor 210 as shown in FIG. 2. However, in other embodiments, the sighting structure 216 may be integrated into the acoustic sensor's body.

The acoustic sensors 210 are attached, via suitable cables 250 (or other suitable device such as a suitable wireless interface), to a computer system 300, which may be any suitable computer system (e.g., a conventional desktop or laptop PC, a server, or a specialized computing device). In particular embodiments, the computer system 300 includes a medical grade power supply, an internal backup battery, an integrated LCD display (e.g., a touch screen display), an analog-digital converter for converting analog signals from the acoustic sensors 210 into digital format (e.g., an IOTech Daqboard 500 data acquisition board), memory, at least one processor coupled to the memory, and an ECG. In various embodiments, the ECG is used to obtain an overall sense of the patient's natural heart function. In various embodiments, the system may include an earpiece for allowing users to hear signals obtained from the acoustic sensors. This may, for example, allow a user to ensure that the acoustic sensors are monitoring the intended signal.

Figure 3:
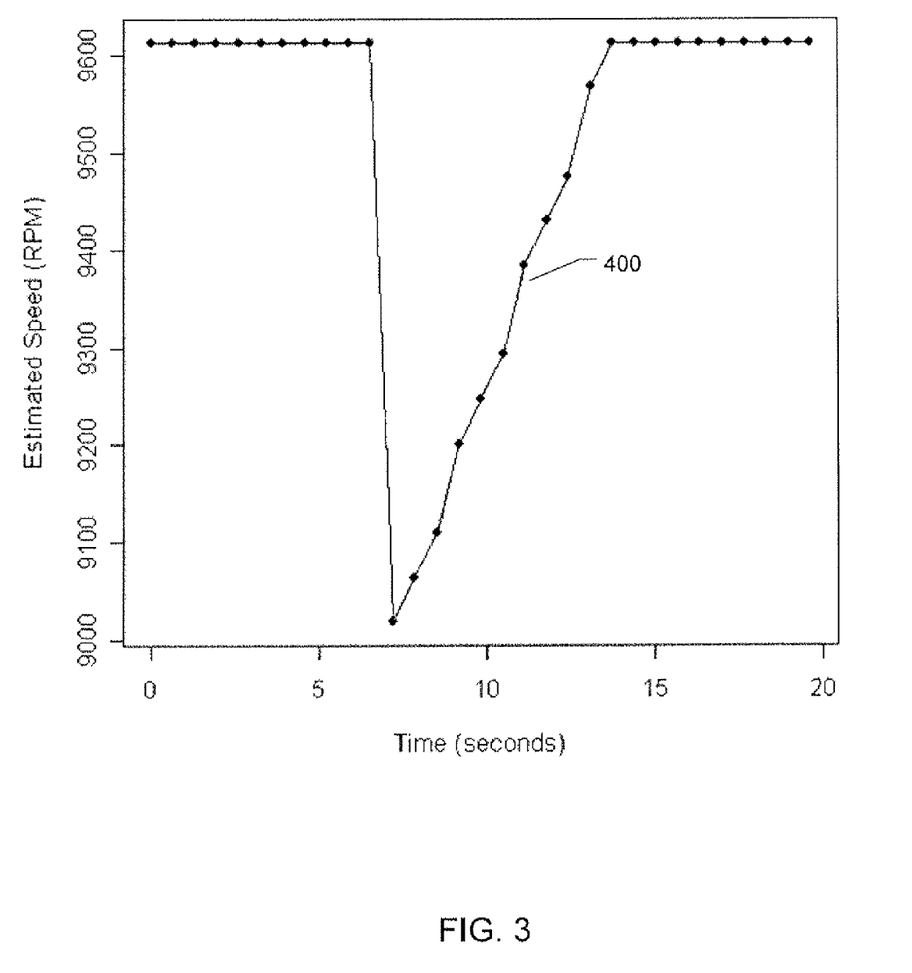

In particular embodiments, the computer system's memory stores a library of acoustic data that corresponds to sounds produced by implanted mechanical devices (e.g., LVAD's of particular makes and models) in various mechanical states. For example, the memory may store acoustic data that corresponds to sounds produced by a HeartMate-H LVAD in the days or weeks before the LVAD suffers a mechanical failure. As another example of the type of data that may be stored in the computer system's library, FIG. 3 shows the acoustic signature of a suction event associated with the Heartmate-II LVAD. As discussed in greater detail below, the computer system 300 may compare data from the system's acoustic data library with data received from the monitoring system's various acoustic sensors 210 to assess the current mechanical state of the LVAD. Different medical devices may have different sound signatures. Accordingly, computer systems according to various embodiments of the invention include an extensive library of sound signatures and/or algorithms that change in size (e.g., increase) over time.

It should be understood that, in various embodiments, the acoustic monitoring system 10 may include one or more networking devices that are adapted for connecting one or more components of the acoustic monitoring system 10 to an external computer network. This may be useful, for example, for transferring data from the acoustic monitoring system 10 to external computers, or for having the acoustic monitoring system 10 receive software updates from an external server. In a particular embodiment, the acoustic monitoring system 10 is adapted for transmitting information from a first location (e.g., a patient's home) to a computer that is located at a second location that is remote from the first location (e.g., a hospital). This may allow a patient to undergo a checkup on her implanted mechanical device without leaving her home.

Use of Various Embodiments of the Acoustic Monitoring System

The use of particular embodiments of the acoustic monitoring system 10 will now be described in greater detail. It should be understood that this disclosure is not limited to the particular uses or techniques described below, which the Applicants regard as exemplary in nature.

To use the acoustic monitoring device of FIG. 1, before a patient's first use of the device, a technician weighs and measures the patient (e.g., the patient's girth) and determines (e.g., based on empirical data and/or the technician's judgment): (1) whether to use the full belt 100 in monitoring the patient; and (2) where the acoustic sensors 210 should be placed on the belt 100 in order to maximize the performance of the acoustic monitoring system 10.

In various embodiments, during visits after the patient's first visit, the patient is weighed and the patient's current weight is used to revise the patient's belt settings. For example, if the patient has gained weight since his last visit, the belt settings may be adjusted to account for the patient's corresponding increase in girth. In particular embodiments, the belt is adapted to apply pressure that serves to urge one or more (and preferably all) of the system's acoustic sensors against the patient's body while the system is in use. The belt may include any suitable mechanism (e.g., springs or resilient foam material) to facilitate this functionality. In various embodiments, the system may include a force feedback mechanism that is adapted to measure the pressure applied by the system's acoustic sensors to the patient's body. This feedback system may, for example, include one or more pressure transducers and a mechanism for conveying information from the pressure transducers to a user. In some embodiments, the feedback system may include a control system that is adapted for automatically maintaining a predetermined pressure between the transducers and the patient.

For example, if the patient is in critical condition, is feeling to ill to sit upright, or particularly obese, the technician may decide not to use the full belt 100 in a particular session with the patient. In such a case, the technician may first detach the belt's first and second lateral support portions 117, 119 from the belt's central support portion 115. The technician may then use belt's central support portion 115 as a hand-held transducer. In particular, the technician may manually position the belt's central support portion 115 proximate to the patient's LVAD device (e.g., over the patient's LVAD pocket), move the central portion's acoustic sensors 210 into the desired positions on the belt's central portion 115, and then use the acoustic sensors 210 on the belt's central support portion 115 to evaluate the patient's LVAD using the techniques discussed in greater detail below.

Alternatively, if the technician decides to use the full belt 100 in the particular session with the patient, the technician wraps the entire belt 100 around the patient's upper or lower thoracic torso as shown in FIG. 1 and fastens the belt 100 so that the belt 100 stays in a substantially fixed position in relation to the patient's chest. The technician then moves belt's acoustic sensors 210 into the desired positions on the belt 100, and then uses the acoustic sensors 210 on the belt's central support portion 115 to evaluate the patient's LVAD using the techniques discussed in greater detail below.

As noted above, in various embodiments, the belt 100 includes graduated markings (e.g., vertical and/or horizontal graduated markings 120, 122), and/or target indicia 127, 128, 129, 131 for assisting a user in positioning acoustic sensors 210 adjacent the belt 100. Also, in particular embodiments, each of the acoustic sensors 210 includes a respective sighting structure 216 that includes a window 215 and a recticle 217 overlaid onto the window 215. In such embodiments, to position an acoustic sensor 210 in a particular position on the belt 100, a technician simply positions the acoustic sensor 210 so that the crosshairs of the acoustic sensor's recticle 217 align with a cross structure of a target indicia 127, 128, 129, 131 that is associated with a particular position on the belt 100. For example, if the technician wishes to place the acoustic sensor 210 of FIG. 2 in position "C", the technician would simply align the crosshairs of the acoustic sensor's recticle 217 with the cross structure of the target indicia 131 that is associated with position C.

In particular embodiments, the acoustic monitoring system 10 is adapted to store, for each test conducted on a particular patient, information regarding the positions of the acoustic sensors 210 on the belt 100 (or other acoustic sensor support device) during the particular test. This can help a technician position the acoustic sensors 210 on the belt in advance of the patient's next visit.

Also, in particular embodiments, the acoustic monitoring system 10 is adapted to suggest alternative positions for the acoustic sensors 210 on the belt 100 (or other acoustic sensor support device) based, for example, on changes in a patient's weight, girth, and/or height that occurred between a previous test and a current test.

Once the acoustic sensors 210 are in place adjacent the patient's body, the technician activates the acoustic monitoring system 10. In a particular embodiment, upon the startup of the acoustic monitoring system 10, the monitoring system's respective acoustic sensors 210 iteratively generate a known sound (e.g., a "chirp", such as a swept-sine signal) that is received by each of the system's other acoustic sensors 210. The system then may then approximate the positions of the various sensors 210 based on: (1) for each sensor 210, the time that a particular chirp was generated by the particular sensor and the time that the "chirp" was received by the monitoring system's other sensors 210; and (2) the circumferential separation of the acoustic sensors 210 (e.g., as determined based on the relative positions of the sensors on the patient's belt). The circumferential separation of the acoustic sensors 210 may, for example, be manually entered into the computer system 300 by the technician if the positions of the acoustic sensors 210 were not determined in advance or otherwise stored in the computer system's memory.

According to one alternative embodiment, the positions of the acoustic sensors 210 may be determined using infrared tracking. In this regard, infrared transducers may be used in conjunction with a series of cameras to determine the position of the acoustic sensors, wherein the transducers may be attached to the body or the belt 100 at various positions. For example, infrared tracking such as the OptiTrack™ system provided by Natural Point, Inc. may be employed. The infrared transducers could also be configured as acoustic sensors to obtain acoustic information in addition to location information. The infrared tracking system may provide accurate location information of the acoustic sensors, but this technique is more complex than the aforementioned techniques and may be more burdensome on the patient (e.g., additional set-up time). The infrared tracking system could be useful for both monitoring medical devices within the body and experimental testing (e.g., phantom studies).

Next, the system's various acoustic sensors 210 continue obtaining information regarding acoustic activity within the patient's body (e.g., at a suitable rate, such as 25 kHz). In various embodiments, the system's sensors 210 obtain this information at least substantially simultaneously (e.g., simultaneously). However, in other embodiments, the system's various sensors 210 may obtain this information in a non-simultaneous fashion.

After, or while, obtaining the information regarding the acoustic activity within the patient's body, each sensor transmits the information to the acoustic monitoring system's computer system 300. The computer system 300 then may, in various embodiments, convert this data from analog format into a digital format. Next, the computer system 300 stores the information in the computer system's memory.

As the computer system 300 receives information from the acoustic sensors 210, the computer system 300 may determine the approximate location of the source of each noise detected by the acoustic sensors 210 based on, for example: (1) acoustic information obtained from the monitoring system's various acoustic sensors 210; and (2) information regarding the respective positions of the acoustic sensors 210. If a particular noise is determined to have been generated by a structure other than the mechanical device (e.g., LVAD) being monitored by the monitoring system 10, in various embodiments, the computer system 300 disregards this noise. Otherwise, the computer system 300 compares the acoustic signature of the noise with acoustic signatures, stored within the computer system's memory, that correspond to particular mechanical states of the mechanical device being monitored.

For example, the memory may compare the acoustic signatures of sounds detected by the system's acoustic sensors 210 with acoustic data that corresponds to sounds produced by a HeartMate-II LVAD in the days or weeks before the LVAD suffers a mechanical failure. If the two acoustic signatures are sufficiently similar, the system may generate a warning to the technician indicating a potential impending mechanical failure of the LVAD device. The system may, for example, display this warning on the system's display monitor. The technician may then arrange for appropriate treatment for the patient.

In various embodiments, the system may also store, and be configured to execute, one or more algorithms that may be used to detect impending or current mechanical device failures (e.g., the impending or current failure of an LVAD). Such algorithms, may be, for example, sequences of steps that the system may execute in order to recognize a certain condition of a mechanical device (e.g., a condition that does not have a single acoustic signature.)

CONCLUSION

Many modifications and other embodiments of the inventions set forth herein will come to mind to one skilled in the art to which these inventions pertain having the benefit of the teachings presented in the foregoing descriptions and the associated drawings. For example, while various embodiments of the acoustic monitoring system 10 described above are described as including a belt 100 to support the system's various acoustic sensors 210, any other suitable type of structure may be used to support the sensors 210. Similarly, although various embodiments of the invention described above include multiple acoustic sensors, other embodiments of the invention may include only one acoustic sensor. Therefore, it is to be understood that the inventions are not to be limited to the specific embodiments disclosed and that modifications and other embodiments are intended to be included within the scope of the appended inventive concepts. Although specific terms are employed herein, they are used in a generic and descriptive sense only and not for purposes of limitation.

The invention claimed is:

1. An apparatus for acoustically monitoring performance of a medical device disposed within a body of a patient, said apparatus comprising:
   a plurality of acoustic sensors, wherein a first acoustic sensor is spaced apart from a second acoustic sensor;
   a belt, said first and second acoustic sensors each adapted to be attached adjacent said belt in one of a plurality of positions, said belt configured to apply pressure that serves to urge at least one of said first or said second acoustic sensor against said body of said patient; and
   a computer system that is connected to receive information from said first and second acoustic sensors, wherein:
      said first acoustic sensor is adapted to receive a first set of acoustic information that corresponds to an acoustic activity within said body of said patient;
      said second acoustic sensor is adapted to receive a second set of acoustic information corresponding to said acoustic activity within said body of said patient;
      said computer system is adapted for:
         (A) receiving said first and second sets of acoustic information, and
         (B) using said first and second sets of acoustic information to calculate location information relating to a location of a source of said acoustic activity.

2. The apparatus of claim 1, wherein said computer system is further adapted for using said location information to assess whether said source of said acoustic activity is said medical device.

3. The apparatus of claim 1, wherein said computer system is further adapted for comparing at least one of said first set of acoustic information or said second set of acoustic information with acoustic information from within a library of acoustic information to assess a current mechanical slate of said medical device.

4. The apparatus of claim 3, wherein said computer system is further adapted for comparing at least one of said first set of acoustic information or said second set of acoustic information with acoustic information from within said library of acoustic information to assess whether at least one of said first set of acoustic information or said second set of acoustic information is indicative of a current or impending mechanical malfunction of said medical device.

5. The apparatus of claim 1, wherein said medical device is a left ventricle assist device.

6. The apparatus of claim 1, wherein said computer system is configured for calculating said location information regarding said location of said source of said acoustic activity based, at least in part, on:
   (A) said first set of acoustic information;
   (B) said second set of acoustic information; and
   (C) information regarding a position of said first sensor relative to said second sensor.

7. The apparatus of claim 1, wherein:
   said belt is adapted to be wrapped around said patient's body while said first acoustic sensor receives said first set of acoustic information and while said second acoustic sensor receives said second set of acoustic information.

8. The apparatus of claim 7, wherein said bell is adapted to maintain said first acoustic sensor in a fixed position relative to said second acoustic sensor while said first sensor receives said first set of acoustic information and while said second acoustic sensor receives said second set of acoustic information.

9. The apparatus of claim 1, wherein:
   said belt comprises a first set of one or more markings and/or target indicia, said first set of markings and or target indicia being adapted to facilitate the attachment of said first acoustic sensor adjacent said bell in a first position; and
   said belt comprises a second set of one or more markings and or target indicia, said second set of markings and/or indicia being adapted to facilitate the attachment of said second acoustic sensor adjacent said bell in a second position.

10. The apparatus of claim 9, wherein:
   said first acoustic sensor comprises a window and a recticle disposed within said window, said recticle being adapted to facilitate positioning said first acoustic sensor in said first position by aligning at least a portion of said recticle with said first set of markings and/or target indicia.

11. The apparatus of claim 10, wherein:
   said second acoustic sensor comprises a window and a recticle disposed within said window, said recticle is adapted to facilitate positioning said second acoustic sensor in said second position by aligning at least a portion of said recticle with said second set of markings and/or target indicia.

12. The apparatus of claim 1, further comprising a third acoustic sensor adapted to receive a third set of acoustic information corresponding to said acoustic activity within said body of said patient, wherein said computer system is adapted for (A) receiving said first, second, and third sets of information, and (B) using said first, second, and third sets of information to calculate location information relating to a location of a source of said acoustic activity.

13. The apparatus of claim 12, wherein said first, second, and third acoustic sensors are positioned in a substantially triangular arrangement with respect to one another.

14. A method of determining information regarding a position of an acoustic activity within a patient's body, said method comprising:
    positioning a plurality of acoustic sensors such that a first acoustic sensor is in a first position relative to said patient's body and a second acoustic sensor is in a second position relative to said patient's body, said first acoustic sensor and said second acoustic sensor attached adjacent a belt, said belt configured to apply pressure that serves to urge at least one of said first or said second acoustic sensor against the patient's body;
    using said first sensor to retrieve a first set of acoustic information that corresponds to said acoustic activity;
    using said second sensor to retrieve a second set of acoustic information that corresponds to said acoustic activity; and
    using said first and second sets of acoustic information, as well as location information regarding a position of said first sensor relative to said second sensor, to calculate information regarding a location of a source of said acoustic activity.

15. The method of claim 14, wherein said acoustic activity corresponds to noise generated by a medical device.

16. The method of claim 15, wherein said medical device is a left ventricle assist device.

17. The method of claim 15, further comprising using said location information to assess whether said source of said acoustic activity is said medical device.

18. The method of claim 15, further comprising comparing at least one of said first set of acoustic information or said second set of acoustic information with acoustic information from within a library of acoustic information to assess a current mechanical state of said medical device.

19. The method of claim 18, further comprising comparing at least one of said first set of acoustic information or said second set of acoustic information with acoustic information from within said library of acoustic information to assess whether said acoustic information is indicative of a current or impending mechanical malfunction of said medical device.

20. An apparatus for acoustically monitoring a performance of a medical device disposed within a body of a patient, said apparatus comprising:
    at least one acoustic sensor;
    a belt, said at least one sensor adapted to be attached adjacent said belt in one of a plurality of positions, said belt configured to apply pressure that serves to urge at least one of said at least one acoustic sensor against said body of said patient; and
    a computer system that is connected to receive information from said acoustic sensor, wherein:
        said acoustic sensor is adapted to receive a set of acoustic information that corresponds to an acoustic activity within said body of said patient; and
        said computer system is adapted for:
        (A) receiving said set of acoustic information, and
        (B) using said set of acoustic information to calculate location information relating to a location of a source of said acoustic activity.

* * * * *